(12) United States Patent
Burg et al.

(10) Patent No.: US 9,528,941 B2
(45) Date of Patent: Dec. 27, 2016

(54) METHOD AND APPARATUS FOR DETERMINING ANALYTE CONCENTRATION BY QUANTIFYING AND INTERPRETING COLOR INFORMATION CAPTURED IN A CONTINUOUS OR PERIODIC MANNER

(71) Applicant: SCANADU INCORPORATED, Moffett Field, CA (US)

(72) Inventors: Bernard Burg, Menlo Park, CA (US); Martin Zizi, Enines (BE); Walter De Brouwer, Los Altos, CA (US); Anthony Smart, Costa Mesa, CA (US)

(73) Assignee: SCANADU INCORPORATED, Sunnyvale, CA (US)

( * ) Notice: Subject to any disclaimer, the term of this patent is extended or adjusted under 35 U.S.C. 154(b) by 0 days.

(21) Appl. No.: 14/639,509

(22) Filed: Mar. 5, 2015

(65) Prior Publication Data

US 2015/0241358 A1  Aug. 27, 2015

Related U.S. Application Data

(63) Continuation-in-part of application No. 14/419,939, filed as application No. PCT/US2013/035397 on Apr. 5, 2013.

(Continued)

(51) Int. Cl.
*G01J 3/46* (2006.01)
*G01N 21/78* (2006.01)
(Continued)

(52) U.S. Cl.
CPC ............ *G01N 21/78* (2013.01); *G01N 21/272* (2013.01); *G01N 21/8483* (2013.01);
(Continued)

(58) Field of Classification Search
CPC ...... G01N 21/78; G01N 21/272; G01N 21/80; G01N 21/251; G01N 33/52; G01J 3/10
See application file for complete search history.

(56) References Cited

U.S. PATENT DOCUMENTS 4,446,232 A   5/1984   Liotta
4,772,561 A   9/1988   Genshaw
(Continued)

FOREIGN PATENT DOCUMENTS

GB   2483482        3/2012
WO   02/13136 A2    2/2002
(Continued)

OTHER PUBLICATIONS

Thomas, Shane; PCT Search Report, App. No. PCT/US2015/19076; Jun. 8, 2015; 11 pages.

(Continued)

*Primary Examiner* — Kara E Geisel
*Assistant Examiner* — Maurice Smith
(74) *Attorney, Agent, or Firm* — Alford Law Group, Inc.

(57) ABSTRACT

In one embodiment, an apparatus for automatic test diagnosis of a test paddle is disclosed. The apparatus comprises a personal computing device including: a camera to capture images over time of test pads of a test paddle, a processor coupled to the camera, and a display device coupled to the processor. The processor analyzes the color changes over time of each test pad to determine a color trajectory over time for each test pad. The processor compares the color evolution trajectory for each test pad with color calibration curves for each test pad to determine an analyte concentration of a test biological sample, such as urine. During the analysis by the processor, the display device displays a user interface with results of the analyte concentration in response to the analysis over time.

21 Claims, 12 Drawing Sheets

Related U.S. Application Data

(60) Provisional application No. 61/680,842, filed on Aug. 8, 2012, provisional application No. 61/948,536, filed on Mar. 5, 2014.

(51) Int. Cl.
  *G01N 21/27* (2006.01)
  *G01N 33/52* (2006.01)
  *G01N 21/84* (2006.01)
  *H04N 5/225* (2006.01)
  *G01N 21/77* (2006.01)
  *G01N 21/80* (2006.01)

(52) U.S. Cl.
  CPC .............. *G01N 33/52* (2013.01); *G01N 21/80* (2013.01); *G01N 2021/7793* (2013.01); *G01N 2021/7796* (2013.01); *H04N 5/2251* (2013.01)

(56) References Cited

U.S. PATENT DOCUMENTS

| | | |
|---|---|---|
| 4,833,088 A | 5/1989 | DeSimone et al. |
| 4,855,109 A | 8/1989 | Muraishi et al. |
| 4,859,612 A | 8/1989 | Cole et al. |
| 4,868,108 A | 9/1989 | Bahar et al. |
| 4,943,522 A | 7/1990 | Eisinger et al. |
| 4,976,923 A | 12/1990 | Lipsky et al. |
| 5,008,080 A | 4/1991 | Brown, III et al. |
| 5,110,550 A | 5/1992 | Schlipfenbacher et al. |
| 5,119,830 A | 6/1992 | Davis |
| 5,120,643 A | 6/1992 | Ching et al. |
| 5,141,850 A | 8/1992 | Cole et al. |
| 5,260,219 A | 11/1993 | Fritz |
| 5,308,775 A | 5/1994 | Donovan et al. |
| 5,360,013 A | 11/1994 | Gilbert |
| 5,408,535 A | 4/1995 | Howard, III et al. |
| 5,470,750 A | 11/1995 | Bar-Or |
| 5,501,837 A | 3/1996 | Sayles |
| 5,569,608 A | 10/1996 | Sommer |
| 5,595,187 A | 1/1997 | Davis |
| RE36,268 E | 8/1999 | Szuminsky et al. |
| 5,976,469 A | 11/1999 | Davis |
| 6,183,972 B1 | 2/2001 | Kuo et al. |
| 6,215,892 B1 | 4/2001 | Douglass et al. |
| 6,249,593 B1 | 6/2001 | Chu et al. |
| 6,514,461 B1 | 2/2003 | Lappe et al. |
| 6,541,266 B2 | 4/2003 | Modzelewski et al. |
| 6,764,825 B1 | 7/2004 | Wang |
| 7,267,799 B1 | 9/2007 | Borich et al. |
| 7,292,718 B2 | 11/2007 | Douglass |
| 7,313,257 B2 | 12/2007 | Roman |
| 7,420,663 B2 | 9/2008 | Wang et al. |
| 7,652,268 B2 | 1/2010 | Patel |
| 7,655,456 B2 | 2/2010 | Oshiman et al. |
| 8,150,115 B2 | 4/2012 | Capewell |
| 8,506,901 B2 | 8/2013 | Chen et al. |
| 8,577,079 B2 | 11/2013 | Cohen et al. |
| 8,889,424 B2 | 11/2014 | Ehrenkranz et al. |
| 2001/0045355 A1 | 11/2001 | Gephart et al. |
| 2002/0086435 A1 | 7/2002 | Fernandez Decastro |
| 2002/0168784 A1 | 11/2002 | Sundrehagen et al. |
| 2003/0235923 A1 | 12/2003 | Jurik et al. |
| 2004/0225223 A1* | 11/2004 | Honda ............. A61B 1/00045 600/476 |
| 2005/0221504 A1 | 10/2005 | Petruno et al. |
| 2006/0292040 A1 | 12/2006 | Wickstead et al. |
| 2007/0026530 A1 | 2/2007 | Wu et al. |
| 2007/0058860 A1 | 3/2007 | Harville et al. |
| 2007/0188759 A1* | 8/2007 | Mehendale .......... G01N 21/251 356/409 |
| 2007/0242877 A1 | 10/2007 | Peters et al. |
| 2008/0023647 A1 | 1/2008 | Patel |
| 2008/0137948 A1 | 6/2008 | Tamagawa |
| 2008/0287316 A1 | 11/2008 | Spivey et al. |
| 2010/0118124 A1 | 5/2010 | Kim et al. |
| 2010/0239137 A1 | 9/2010 | Pugia et al. |
| 2011/0111522 A1 | 5/2011 | Zimmerie et al. |
| 2011/0213664 A1 | 9/2011 | Osterhout et al. |
| 2012/0063652 A1 | 3/2012 | Chen et al. |
| 2012/0236308 A1 | 9/2012 | Satoh |
| 2013/0052655 A1 | 2/2013 | Kobayashi et al. |
| 2013/0130398 A1* | 5/2013 | Zang .................... G01N 21/78 436/128 |
| 2013/0273528 A1 | 10/2013 | Ehrenkranz |
| 2013/0303869 A1 | 11/2013 | Rebec et al. |
| 2014/0001058 A1 | 1/2014 | Ghaffari et al. |
| 2015/0055134 A1 | 2/2015 | Papautsky et al. |

FOREIGN PATENT DOCUMENTS

| | | |
|---|---|---|
| WO | 2010/118124 A2 | 10/2010 |
| WO | 2011/089094 A1 | 7/2011 |
| WO | 2013/064054 A1 | 5/2013 |
| WO | WO2013116831 | 8/2013 |
| WO | 2014/025415 A2 | 2/2014 |
| WO | WO2014025415 | 2/2014 |

OTHER PUBLICATIONS

Lapresta-Fernandez, et al., Environmental Monitoring Using A Conventional Photographic Digital Camera For Multianalyte Disposable Optica Sensors, Analytica Chimica Acta, Aug. 23, 2011, pp. 328-337, vol. 706, 0 No. 2, Elsevier, Amsterdam, Netherlands; 11 pages.

Garcia, et al., Mobile Phone Platform As Portable Chemical Analyzer, International Journal Devoted To Research And Development of Physical and Chemical Transducers, Apr. 17, 2011, pp. 350-359, vol. 156, No. 1, Elsevier SA, Switzerland; 12 pages.

Hirayama, et al., Visual and Colorimetric Lithium Ion Sensing Based on Digital Color Analysis, Analytical Chemistry, Feb. 1, 2000, pp. 465-474, vol. 72, No. 3, American Chemical Society, U.S.; 10 pages.

Martinez, et al., Simple Telemedicine for Developing Regions: Camera Phones and Paper-Based Microfluidic Devices for Real-Time, Off-Site Diagnosis, Analytical Chemistry, Aug. 15, 2008, pp. 3699-3707, vol. 80, No. 10, American Chemical Society, U.S.; 9 pages.

Lee, et al., A Simple and Smart Telemedicine Device for Developing Regions: A Pocket-Sized Colorimetric Reader, Lab On A Chip, Jan. 7, 2011, pp. 120-126, vol. 11, No. 1, Royal Society of Medicine; 7 pages.

\* cited by examiner

METHOD AND APPARATUS FOR DETERMINING ANALYTE CONCENTRATION BY QUANTIFYING AND INTERPRETING COLOR INFORMATION CAPTURED IN A CONTINUOUS OR PERIODIC MANNER

CROSS REFERENCE TO RELATED APPLICATIONS

This application claims the benefit of U.S. Provisional Patent Application No. 61/948,536 entitled APPARATUS FOR DETERMINING ANALYTE CONCENTRATION BY QUANTIFYING AND INTERPRETING COLOR INFORMATION CAPTURED IN A CONTINUOUS OR PERIODIC MANNER filed Mar. 5, 2014 and incorporated herein by reference.

This application further is a continuation in part claiming the benefit of U.S. patent application Ser. No. 14/419,939 entitled METHOD AND APPARATUS FOR PERFORMING AND QUANTIFYING COLOR CHANGES INDUCED BY SPECIFIC CONCENTRATIONS OF BIOLOGICAL ANALYTES IN AN AUTOMATICALLY CALIBRATED ENVIRONMENT filed Feb. 6, 2015. U.S. patent application Ser. No. 14/419,939 is a national phase application claiming priority to Patent Cooperation Treaty (PCT) Application No. PCT/US2013/035397 entitled METHOD AND APPARATUS FOR PERFORMING AND QUANTIFYING COLOR CHANGES INDUCED BY SPECIFIC CONCENTRATIONS OF BIOLOGICAL ANALYTES IN AN AUTOMATICALLY CALIBRATED ENVIRONMENT filed Apr. 5, 2013. PCT Application No. PCT/US2013/035397 claims the benefit of U.S. Provisional Patent Application No. 61/680,842 entitled MULTI-ANALYTE RAPID DIAGNOSTIC TEST AND METHOD OF USE filed Aug. 8, 2012.

FIELD

The invention generally relates to methods and apparatus for determining a diagnosis from a diagnostic test device.

BACKGROUND

Reagent dipsticks and immunoassays have been used in medical clinics for decades in connection with methods for rapidly diagnosing health conditions at the point of care. Dipsticks have been used for the diagnosis of a number of conditions including urinary tract infections, preeclampsia, proteinuria, dehydration, diabetes, internal bleeding and liver problems.

Dipsticks are laminated sheets of paper containing reagents that change color when exposed to an analyte solution. Each reagent test pad on the dipstick is chemically treated with a compound that is known to change color in the presence of particular reactants. For example. in the context of a urinalysis, the dipstick will typically include reagent pads for detecting or measuring an analyte present in a biological sample of urine.

The magnitude of the color change of the reagent test pads is proportional to analyte concentration in the biological sample fluid. Dipsticks and their reagent test pad are typically manually interpreted with the naked eye by comparing the test strip against a colored reference chart. Such manual color comparisons can be imprecise for several reasons, including; changes in ambient lighting, subjective comparisons, and impaired color vision that a significant portions of the earth's population has.

It is desirable to improve upon manual color comparisons between reagent test pads and color reference charts.

BRIEF SUMMARY

Some embodiments of the invention relate generally to systems and methods for automatically detecting the presence or absence of a color in a camera field. Other embodiments of the invention relate generally to systems and methods for automatically detecting the color variation during a period of time or color evolution over time. Still other embodiments of the invention relate generally to systems and methods for automatically providing color vision, color recognition, and color corrections. When in controlled lighting conditions or closed systems lighting environments, color matching and color corrections are known in the art, however when operating in uncontrolled lighting environments these operations are significantly more complex for humans as well as machines.

Embodiments of the invention relate to methods for detecting the presence or absence of colors in samples or in any chemical reactions that could be photometrically time-resolved. More specifically embodiments of the invention detect and classify color changes in medical applications. Users dip reagent dipsticks into fluid samples and a device is used to quantify the colors of the resulting reaction. The quantified colors correlate to analyte concentrations which are then analyzed and displayed by one or more electronic devices. By quantifying the color change using an apparatus instead of the human eye, errors linked to a user's color vision are removed from results. Around 8% of men and 0.5% of women have some color perception limitation. In addition, the apparatus and methods also remove subjective errors that may occur when a human being compares a color reagent test pad against a printed reference color scale. Other errors that may be resolved include poor rendering of the reference color scales and errors due to gloss or texture differences, etc.

DETAILED DESCRIPTION

Figure 1:
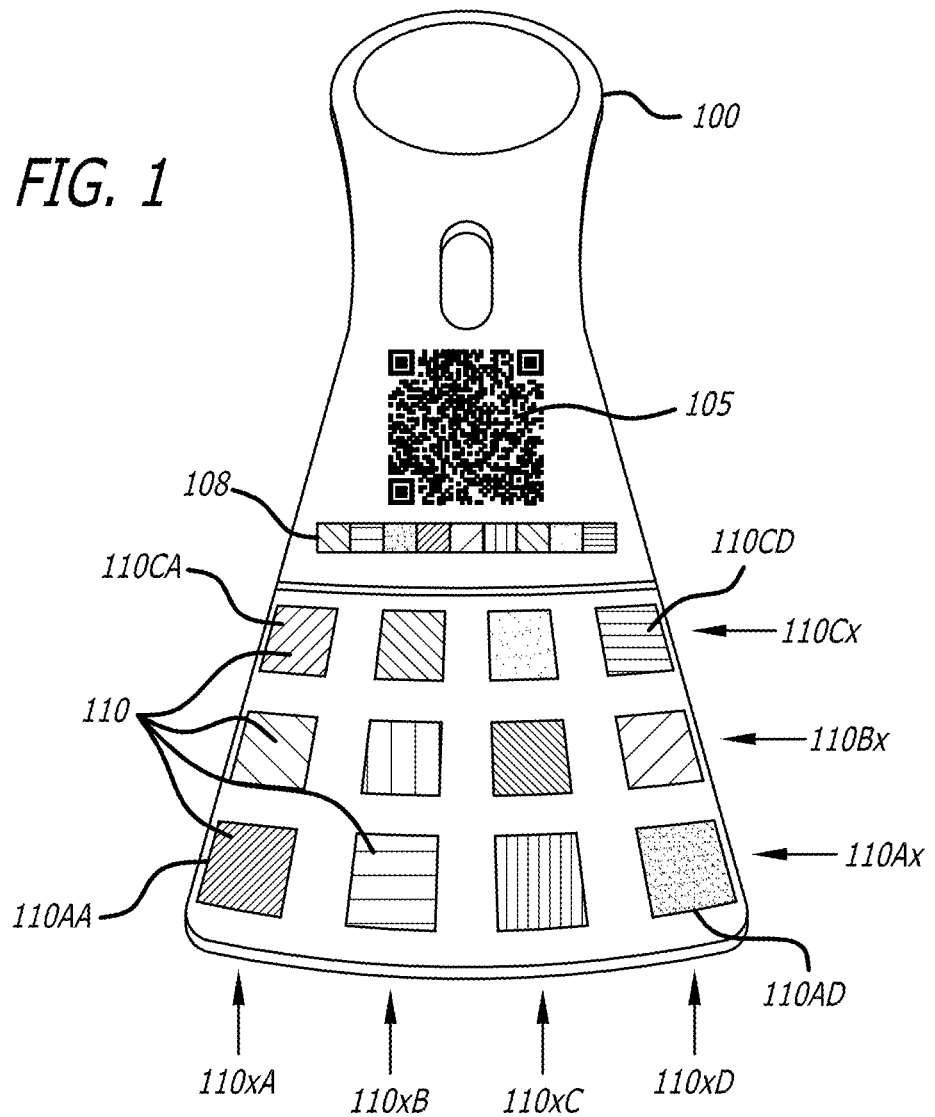
FIG. 1 is a top view of a diagnostic test device (test paddle) with a plurality of reagent test pads to provide a system for analyzing a biological sample over time.

In the following detailed description of the embodiments of the invention, numerous specific details are set forth in order to provide a thorough understanding of the present invention. However, it will be obvious to one skilled in the art that the embodiments of the invention may be practiced without these specific details. In other instances well known methods, procedures, components, and circuits have not been described in detail so as not to unnecessarily obscure aspects of the embodiments of the invention.

The embodiments of the invention includes a method, apparatus and system to analyze observe and quantify photometric reactions over a period of time.

Introduction

Reagent dipsticks and immunoassays have been used in medical clinics for decades in connection with methods for rapidly diagnosing or monitoring health conditions at the point of care or at the doctor's office.

In particular, in a clinical environment, dipsticks have been used for the diagnosis of urinary tract infections, preeclampsia, proteinuria, dehydration, diabetes, internal bleeding and liver problems. As is known, dipsticks are laminated sheets of paper containing reagents that change color when exposed to an analyte-containing solution. Each reagent test pad on the dipstick is chemically treated with a compound that is known to change color in the presence of particular reactants. For example, in the context of a urinalysis, the dipstick will include reagent pads for detecting or measuring analytes present in a biological sample, in this case urine, including glucose, bilirubin, ketones, specific gravity, blood, pH, protein, urobilinogen, nitrite, leukocytes, microalbumin and creatinin. Biomarkers for drug use monitoring, Prostate Specific Antigen (PSA) for prostate cancer, etc., have also been set up in dry solid chemical test pads.

One automatic method for interpreting test results of dipsticks and immunoassays, which have been exposed to a sample solution, is shown for example, by U.S. Patent Application Publication No. 2012/063652 to Chen et. al (hereinafter "the Chen '652 publication". The Chen '652 publication discloses a method for color-based reaction testing of biological materials, albeit in an un-calibrated environment, by capturing a digital image of both a test strip and a colored reference chart side by side in a single image. The test results for the test strip are automatically obtained by performing simple color matching between the reacted regions of the test strip and the color reference chart to determine analyte concentration of the biological material.

However, existing assays tend to perform their color matching analysis at only a single point in time. As such these machines base their analysis on a snapshot and neglect the rate of color change. Accordingly, existing assays cannot report back on secondary reactions or intermediate reaction rates.

A platform of generic color vision tools has been developed to address most of the problems described in the state of the art. Some of these problems have been described in International Patent Ap. No. PCT/US2013/035397, Publication No. WO 2014025415 A2, filed on Aug. 5, 2013 by Bernard Burg et al. (incorporated herein by reference) (hereinafter Burg '397), as applied to the particular application performing and quantifying color changes induced by specific concentrations of biological analytes in an automatically calibrated environment.

Analytes of urine reagent strips for urinalysis have different reaction times, for example reagents of most dipstick manufacturers report the following reading times corresponding to the completion of the chemical reaction: glucose, bilirubin, microalbumin, and creatinin at thirty seconds (s); ketones at forty seconds, specific gravity at forty five seconds; blood, pH, protein, urobilinogen, and nitrite at sixty seconds; and leukocytes at one hundred twenty seconds.

Existing automatic urinalysis machines read all these values at the same time, around sixty seconds after dipping the reagent strips into urine. As such. these machines base their analysis on a snapshot and neglect the speed rate of color changes, thus they cannot report back on secondary reactions nor intermediate reaction rates. For the particular case of leukocytes, automatic readers need to anticipate the final colors reached after one hundred twenty seconds, based on the colors present at sixty seconds. This estimation is based on the chemical reaction rate.

Solution

The embodiments of the invention include a method and apparatus that continuously or periodically monitors the color changes of reagent test pads over time of the chemical reactions with a biological sample. Each of a plurality of the reagent test pads (e.g.—glucose, bilirubin, ketones, specific gravity, blood, acidity pH, protein, urobilinogen, nitrite, leukocytes, microalbumin and creatinine) is individually monitored to provide an optimal color interpretation in near-real time. Color interpretation is augmented by taking a color time-gradient into account. A chemical reaction rate model is approximated to yield a higher interpretation precision of color interpretation.

Embodiments of the invention also provide improved accuracy through better color correction, and error reduction using statistical methods to cross reference common factors such as time, temperature, and acidity (pH) of chemical reactions on chemical test pads on a paddle.

Precision/accuracy is improved by individually modeling the chemical reaction rate of each chemical test pad (CTP), and providing better color correction and superior reaction calibrations. A sequence of color images over time are used to interpret color instead of a single image.

Chemical reactions of CTPs on the same test paddle can be cross-referenced to each other. The individual chemical reactions analyzed of CTPS on the same test paddle share a same reaction duration, temperature, and acidity (pH). Thus, the naive independent interpretation of the chemical reactions can be enhanced by mathematical equations sharing duration, temperature, and pH amongst the reactions. Cross-referencing the chemical reactions on the CTPS can mathematically reduce the error ranges of the application through known statistical methods.

Some embodiments of the invention also provide a user friendly interactive user interface. A user interface is provided to hold user attention with real-time interpretations. The user interface allows users to observe the reagents reactions through an augmented reality, helping them to continue focusing their attention to the process while gratifying them with a superior interactive experience.

A platform of generic open photometry tools is disclosed herein to address a number of problems described in the state of the art. As defined herein, open photometry is a photometer that does not require shielding from interfering photonic pollution, hence open photometers do not require an enclosure with a fixed light path. Problems such as ambient light levels, fluid sample handling, and color correction have been described in Burg '397, as applied to the particular application for performing and quantifying color changes induced by specific concentrations of biological analytes in an automatically calibrated environment.

In particular, the methods described in Burg '397 for working in uncontrolled lighting conditions include capturing color images by making geometric corrections, performing color corrections, establishing color calibration trajectories, and comparing colors taken in uncontrolled lighting conditions to the established color trajectories.

One aspect of embodiments of the invention augments the existing capabilities of the method and device described in Burg '397 by extending the apparatus towards a portable device or head-mounted device capable of capturing sequences of images and displaying the progress of the reactions and results therefrom in near-real time. When using a portable electronic device to capture images of the paddle 100, the images are captured without controlled lighting conditions or closed system lighting environments. Color matching and color corrections are significantly more complex when trying to capture images in uncontrolled lighting environments. Thus, sequences of images of the changing color of test pads are captured at a plurality of time points and analyzed by the embodiments of the invention to improve diagnostic results of measured concentrations of various analytes in a biological sample.

Another aspect of some embodiments of the invention is to augment the reality perceived by a user by processing the perceived sequence of images and displaying the progress of the reactions in near-real time on a head-mounted display and image capturing device.

FIG. 1 illustrates a diagnostic instrument paddle (test paddle) 100. A similar diagnostic test paddle was described in Burg '397. In this embodiment, paddle 100 has twelve reagent pads 110. The twelve reagent pads 110, also referred to as chemical test pads (CTP) or simply test pads, are positioned near the bottom of the paddle 100. As the CTPs 110 undergo chemical reactions with an applied biological sample, they change color over time in response to concentrations of various analytes in the biological sample.

In this exemplary embodiment the CTPs 110 are arranged in three rows (110Ax-110Cx) and four columns (110xA-110XD). Each CTP may be treated with a chemical compound (a reagent) specifically selected to react with a specific analyte.

The paddle 100 may include a unique identification such as a Quick Response (QR) code 105 to automatically identify the test paddle 100. The QR code 105 may be configured to contain certain identification information about the paddle 100, such as a list of the analytes that are being tested, expiration date of the paddle 100, the conditions that are being tested, and other identifying information. The information may be printed directly on the unique identification or encrypted within the QR code 105.

Alternatively, the QR code 105 may be associated with information stored elsewhere, such as is the case with bar codes or other short distance data exchange devices and methods. The identification information may be used in validation processes to ensure the diagnostic paddle 100 is suitable for the tests being performed and to ensure that it is safe to use, in good working condition, or to resolve other issues which may impact quality and reliability of the test results.

The test paddle 100 may also include a reference color bar (RCB) 108. The RCB 108 includes a plurality of color samples in a side-by-side linear arrangement. For example, the RCB 108 may include color samples for one or more of the following colors: Cyan, Magenta, Yellow, Key (black), Gray, White, Red, Green, and Blue. The color sample colors correspond with common color spaces, such as Red-Green-Blue or Cyan-Magenta-Yellow-Key (black). The RCB 28 is used for image processing, specifically to calibrate a digital image to improve the quality and accuracy of color analysis.

As mentioned above, a portable electronic device, that may include a head mounted device, is the preferred device for capturing a color digital image of the test paddle 100. In some embodiments of the invention, an image of paddle 100 is displayed on the portable electronic device with information and instructions for the user.

Figure 2:
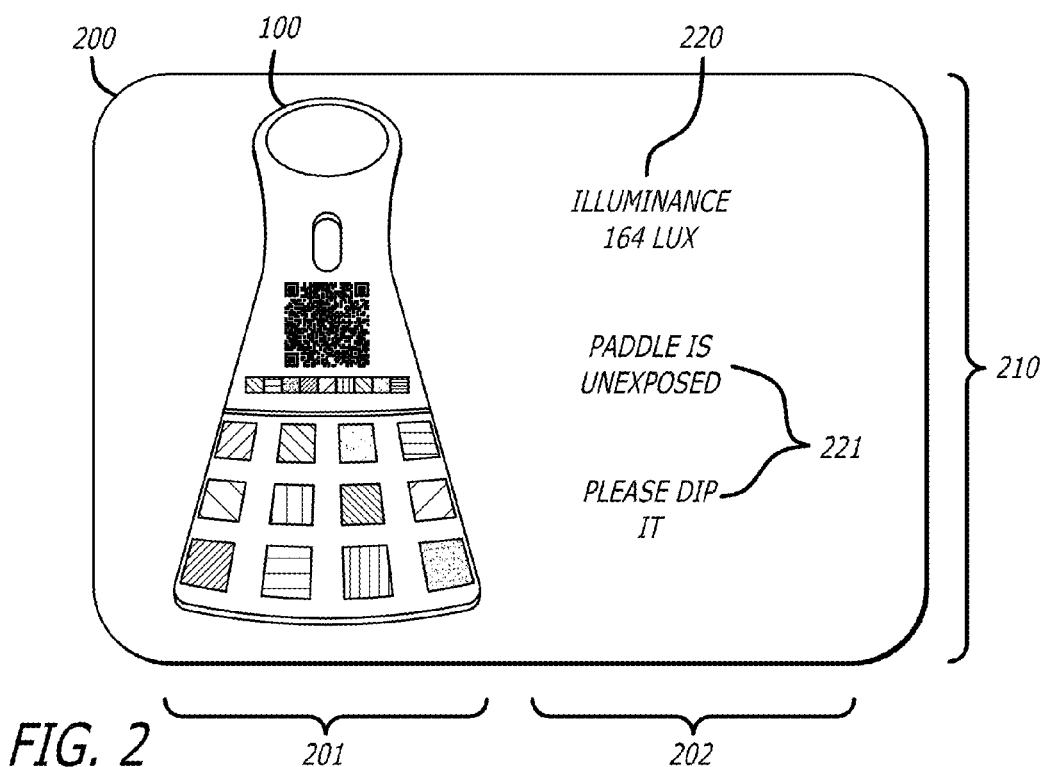
FIG. 2 is an exemplary display of a vision field showing reagent test pads of the diagnostic test device (test paddle) on the left side of the display and information and instructions are shown on the right.

FIG. 2, for example, illustrates a field of view or vision field 200 with the test paddle 100 displayed in one side 201 of the vision field 200 and a user interface (UI) 210 displayed in an opposite side 202 of the vision field 200. The user interface 210 automatically provides instructions, information, and results of the color analysis of the CTP 110 as they undergo chemical reactions.

The vision field 200 may be captured, displayed, and analyzed by a number of devices. However, it is desirable to make the testing and results personal and convenient by integrating the capture, display, and analysis into a user operable system so that the user can test and obtain his/her own results. One system for capture, display and analysis is an augmented reality device that augments the reality perceived by a user by providing the vision field 200.

Figure 10A:
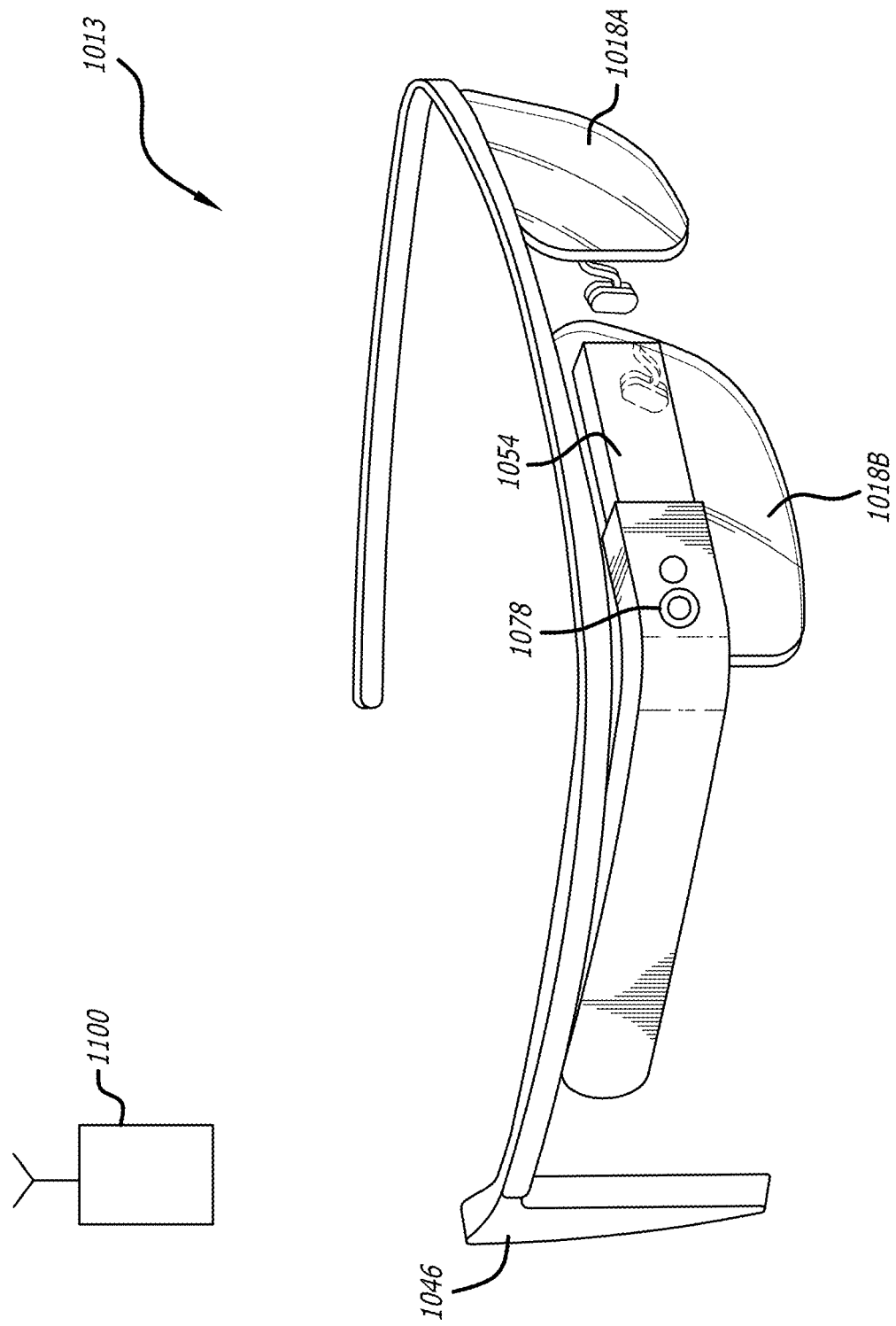
FIG. 10A is a perspective view of an exemplary electronic device of a system for analyzing biological samples over time.

Briefly referring to FIG. 10A, one such augmented reality device may be eye glasses or goggles 1013 that provides a heads up display of images projected against an eye glass (lens) 1018B or provides a small display device screen 1054 that displays images through the eye glass 1018B. Eyeglasses or goggles 1013 with small display devices are further shown and described in US Patent Application Publication No. 2013/0235331A1, entitled EYEGLASS FRAME WITH INPUT AND OUTPUT FUNCTIONALITY, filed by Mitchell Joseph Heinrich et al on Mar. 2, 2012, which is incorporated herein by reference. One eye glass (lens) 1018A may not have a display device screen so that the user may better visualize the physical location of test paddle 100.

The eye-glasses or goggles 1013 may be used to capture an image or a series of images to time resolve the chemical reactions occurring on the CTPs 110. Use of a head mounted camera 1078 alleviates some of the problems found while handling biological samples and concurrently trying to capture video with a hand held device. Goggles 1013 augment the testing experience by providing information such as illuminance (or luminous emittance) and elapsed time to the user during stages of the analyte testing. Instructions are also given to the user, during stages of the analyte testing, to focus the user's attention onto particular CTPs that are undergoing chemical reaction. The instructions may be displayed to the user on the display device screen 1054 or projected on the eyeglass 1018B. Alternatively, an earpiece or earphone 1046 may be used to audibly communicate instructions to the user.

Figure 11:
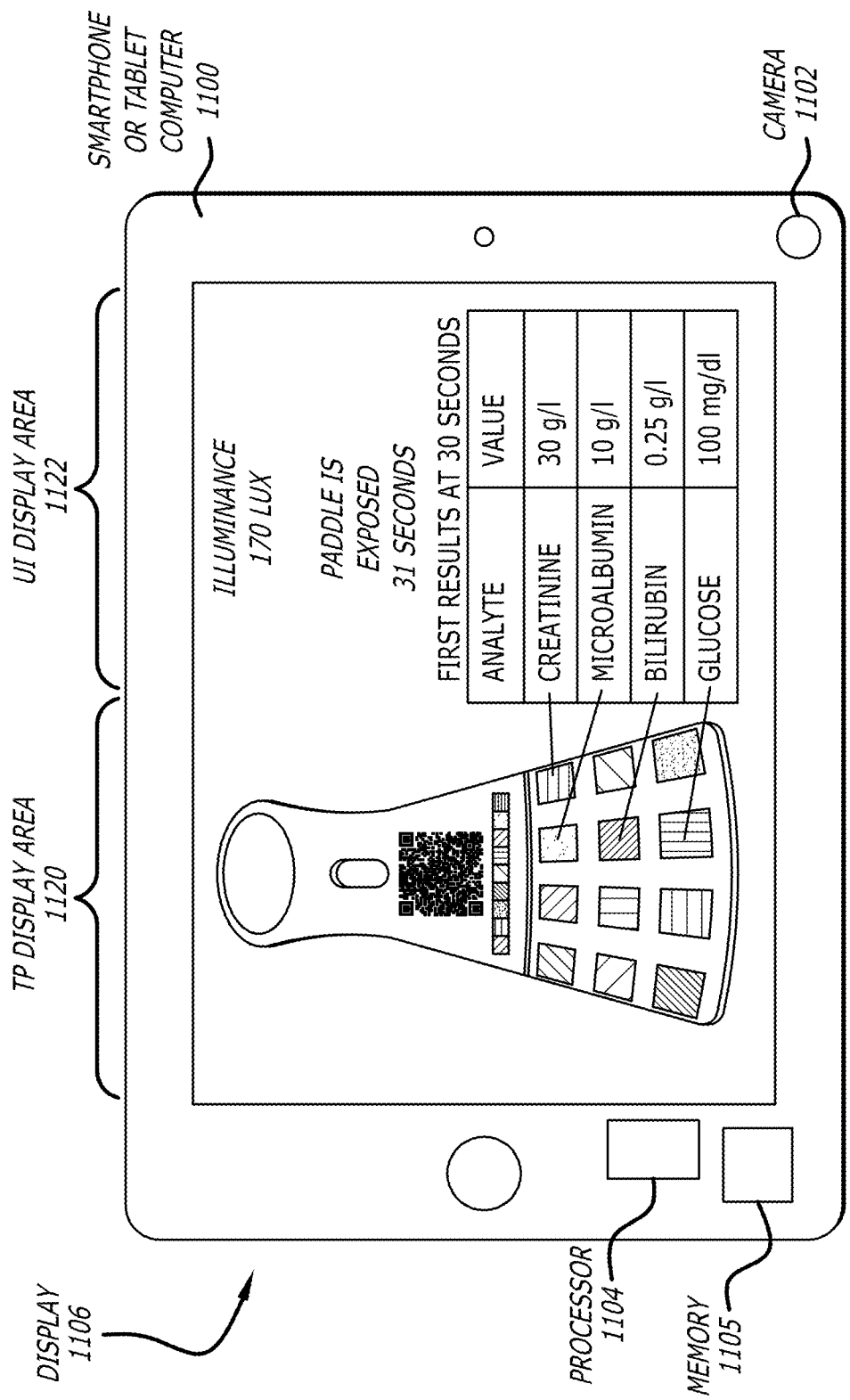
FIG. 11 is top view of a yet another exemplary electronic device of a system for analyzing biological samples over time.

The eye-glasses or goggles 1013 may be in communication with a smartphone or tablet computer 1100 such as shown in greater detail in FIG. 11. The eye-glasses or goggles 1013 may wirelessly via wireless communication channel (e.g., Bluetooth, Wi-Fi) or wired via cable (e.g., USB cable) to communicate graphical images periodically to the smartphone or tablet computer 1100. In this embodiment, the smartphone or tablet computer 1100 includes a processor 1104 and a memory 1105 to store instructions for execution by the processor. The instructions may be software that performs the algorithms and the methods described herein to obtain results. The instructions may further generate the pixels of the user interface for display by the display device of the goggles 1013. The computer 1100 may communicate the results and the user interface to the goggles 1013 for display to the user.

Figure 10B:
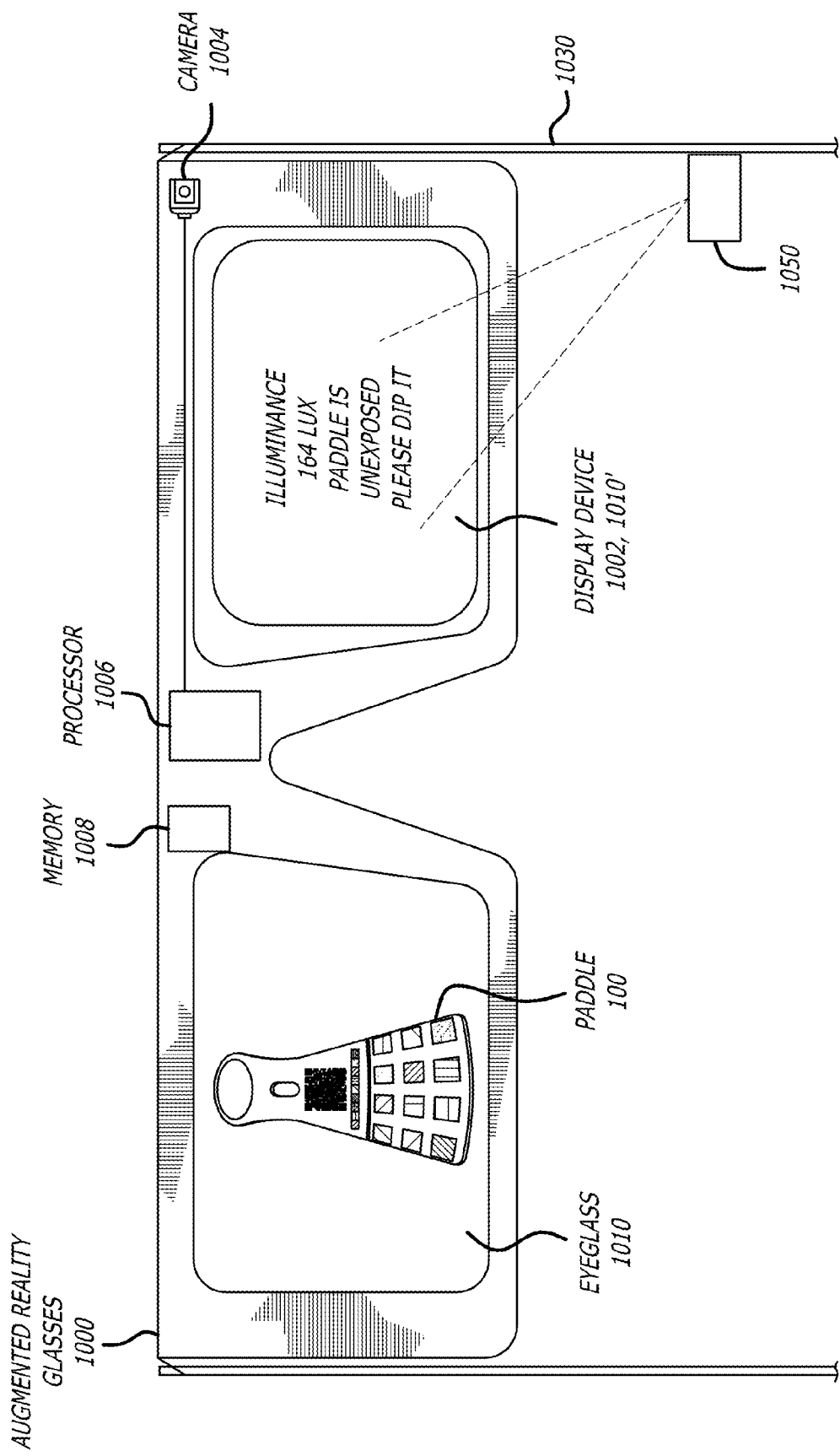
FIG. 10B is side view of an exemplary electronic device of a system for analyzing biological samples over time.

In FIG. 10B, a front view of another exemplary augmented reality glasses/goggles 1000 is illustrated. The goggles 1000 includes a memory 1008 and a processor 1006 coupled together. A camera 1004 coupled to the processor is used to capture images of a test paddle 100 and its test pads during reaction to a sample. In this example, instead of being displayed side by side, information and instructions about the test is displayed by a small display device 1002 coupled to the processor 1006 that is located in one of the user's eyepieces. The other eyepiece has an eyeglass or lens 1010 that may be transparent to allow the user to see paddle 100 during the reaction. Preferably, the camera 1004 is mounted to or integral with goggle 1000, however some Heads-Up-Display (HUD) devices may not include an integrated camera. In such cases, another image capture device connected to a processor may be used to capture images of the reaction for analysis by the processor without deviating from the scope of this invention.

In an alternate embodiment, the display device 1002 is substituted by a lens 1010' that can receive a projected image from a projecting device 1050 mounted to the eyeglass frame (a temple portion 1030 thereof) of the goggles 1000 and coupled to the processor 1006.

Alternatively, FIG. 11 illustrates another electronic device with a camera that may be used with the diagnostic paddle 100 to obtain results. A smartphone or tablet computer 1100 having a camera 1102 and a display device 1106 may be used to obtain results from the diagnostic paddle 100. The display device 1106 may provide a split screen with a test paddle display area 1120 to display the test paddle 100 and a user interface display area 1122 to display instructions and results to the user. The smartphone or tablet computer 1100 further includes a processor 1104 and a memory 1105 to store instructions for execution by the processor. The instructions may be software that provide the user interface in the UI display area 1122 and performs the algorithms and the methods described herein to obtain results.

Reference is now made to FIG. 2. For eye glasses or goggles with a heads up display, the left part 201 of the vision field 200 presented to a user, is the test paddle 100 described herein with reference to FIG. 1. In the right side 202 of the vision field 200, a small screen by means of projection or display device, displays information 220 calculated from the test pads 110 of the paddle 100. Those skilled in the art will recognize that the left and right side vision fields may be interchanged.

In response to the color change caused by chemical reaction of the reagent in the CTPs 110 of the paddle 100, information 220 may be calculated by the methods described in Burg '397, which is incorporated herein by reference. Instructions 221 (part of the user interface 210) may be displayed on the small display screen to the user to guide him/her through the protocol or procedures for obtaining information from the test pads 110 of the diagnostic instrument paddle 100. The instructions 221 may indicate to the user the test paddle 100 is unexposed to the biological sample. The instructions 221 may further instruct the user to expose the CTPs of the test paddle such as by dipping it into the biological sample and starting a timer associated with an electronic device.

Figure 3:
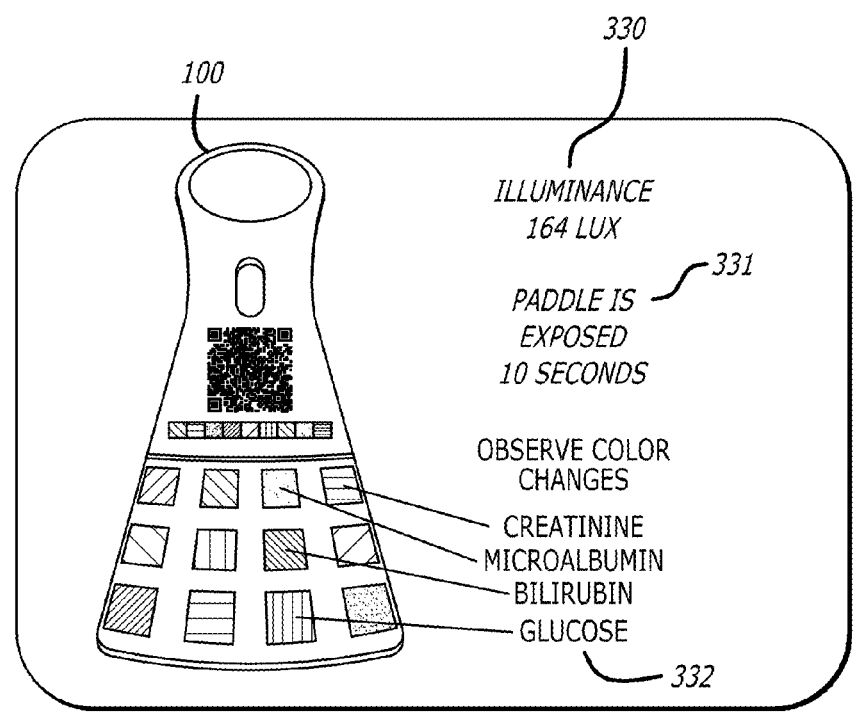
FIG. 3 is an exemplary display of a vision field showing the diagnostic test device (test paddle) with its reagent test pads after a time lapse of 10 seconds.

FIG. 3 illustrates a real-time interpretation of the data as it may appear in an augmented reality device. The augmented reality device may display an image of the paddle 100 alongside additional information. On the left side of the vision field, the user sees the paddle 100 and the CTP chemical reaction colors evolving over time. On the right side of the vision filed the user may be presented with pertinent information about the medical analysis the user is conducting. For example, the augmented reality information may present the illuminance measurement (or luminous emittance measurement) 330 and the elapsed time 331 since dipping the paddle. In addition the augmented reality device may provide instructions 332 to the user to observe the color changes in faster chemical reactions such as for creatinine, microalbumin, bilirubin, and glucose, for example, that may take place at the CTPs. The real-time interpretation puts a focus on the faster chemical reactions allowing users to follow the quick reactions.

Figure 4:
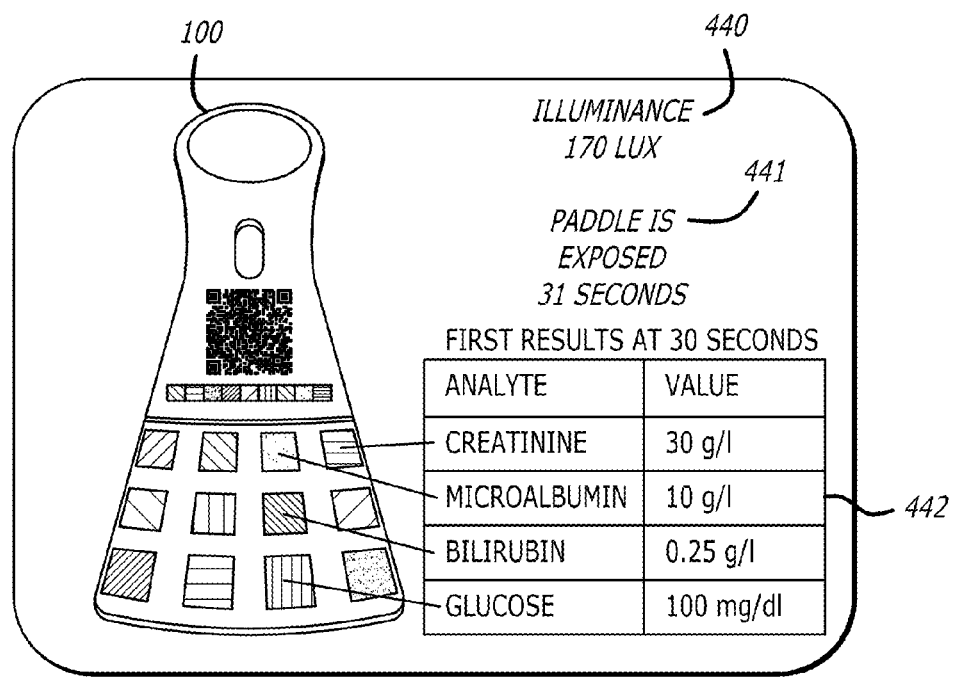
FIG. 4 is an exemplary display of a vision field showing the diagnostic test device (test paddle) with its reagent test pads after a time lapse of 30 seconds.

FIG. 4 illustrates an overview of a first result interpretation. When the method reaches the first timeline for results interpretation, an initial table of results is shown. FIG. 4 shows the paddle at the left side of the visual field. The right side of the visual field adds augmented information such as an illuminance measurement (or luminous emittance measurement) 400 and an elapsed time 441 since dipping the paddle into the reagent. A table 442 illustrates the first results at thirty seconds for example. These are the results for the fast reactions. Similar results may be produced for all chemical reactions, therefore guiding the user in understanding the color recognition process of the CTPs.

Other visual clues may be generated and displayed to a user. For example, visual clues may be provided to the user so that he/she can gain a measure of the overall progress of the chemical reaction at a CTP, as well as a measure of the gradient of these reactions based on the speed of color transformation.

Figure 5:
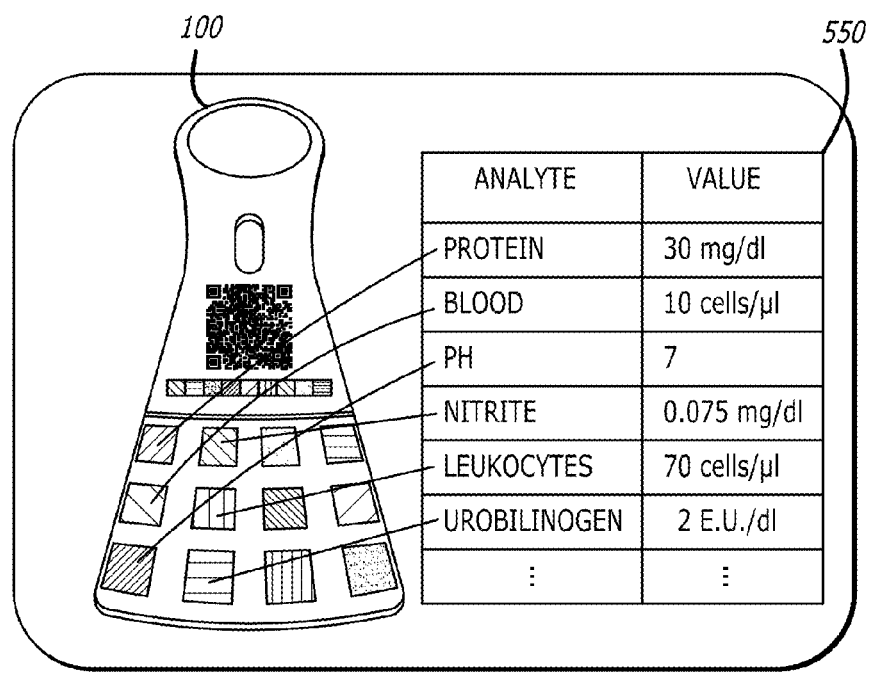
FIG. 5 is an exemplary display of a vision field showing the diagnostic test device (test paddle) with its reagent test pads and a chart of analyte concentrations.

Referring now to FIG. 5, the test paddle 100 is shown after sufficient time has passed wherein all reactions are completed on the CTPs. A table 500, indicating results of the medical analysis, is provided in the right field vision by the small screen display device. These results allow users to understand the process as well as to easily share the results with a medical support team.

Precision of Individual Analyte Reactions

Figure 6A:
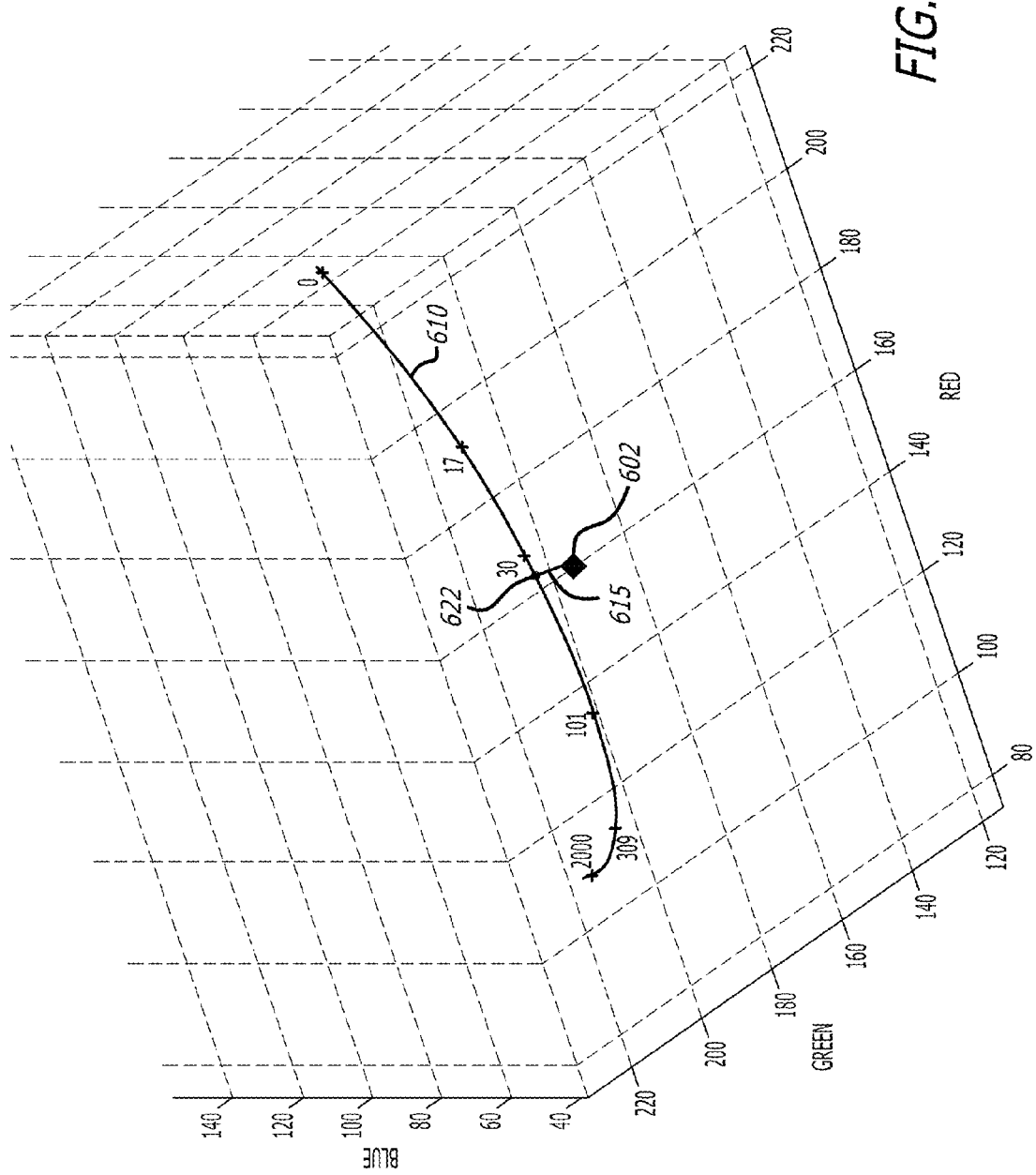
FIG. 6A is a three dimensional red, green, blue (RGB) color space graph of an analyte calibration curve.

Referring now to FIG. 6A, a three dimensional graph of a color calibration curve 610 for an exemplary analyte is shown with red (R), green (G), and blue (B) color axes in RGB space. Current devices for obtaining results from the paddle 100, such as those described in Burg '397, take a single snapshot of the reagent color pads around sixty (60) seconds after dipping the reagent strips into urine. As such, the precision of a measurement around sixty seconds is given by a distance along a projection 615 between the single measurement point 602 in the RGB space and the titration point 622 on the color calibration curve 610 of the analyte. Use of a single snapshot of the color of the reagent color pads at a single time point of sixty seconds may result in an ambiguous determination of concentration, particularly if the environment is not well controlled, such as when it is desirable to provide private in-home testing.

Figure 6B:
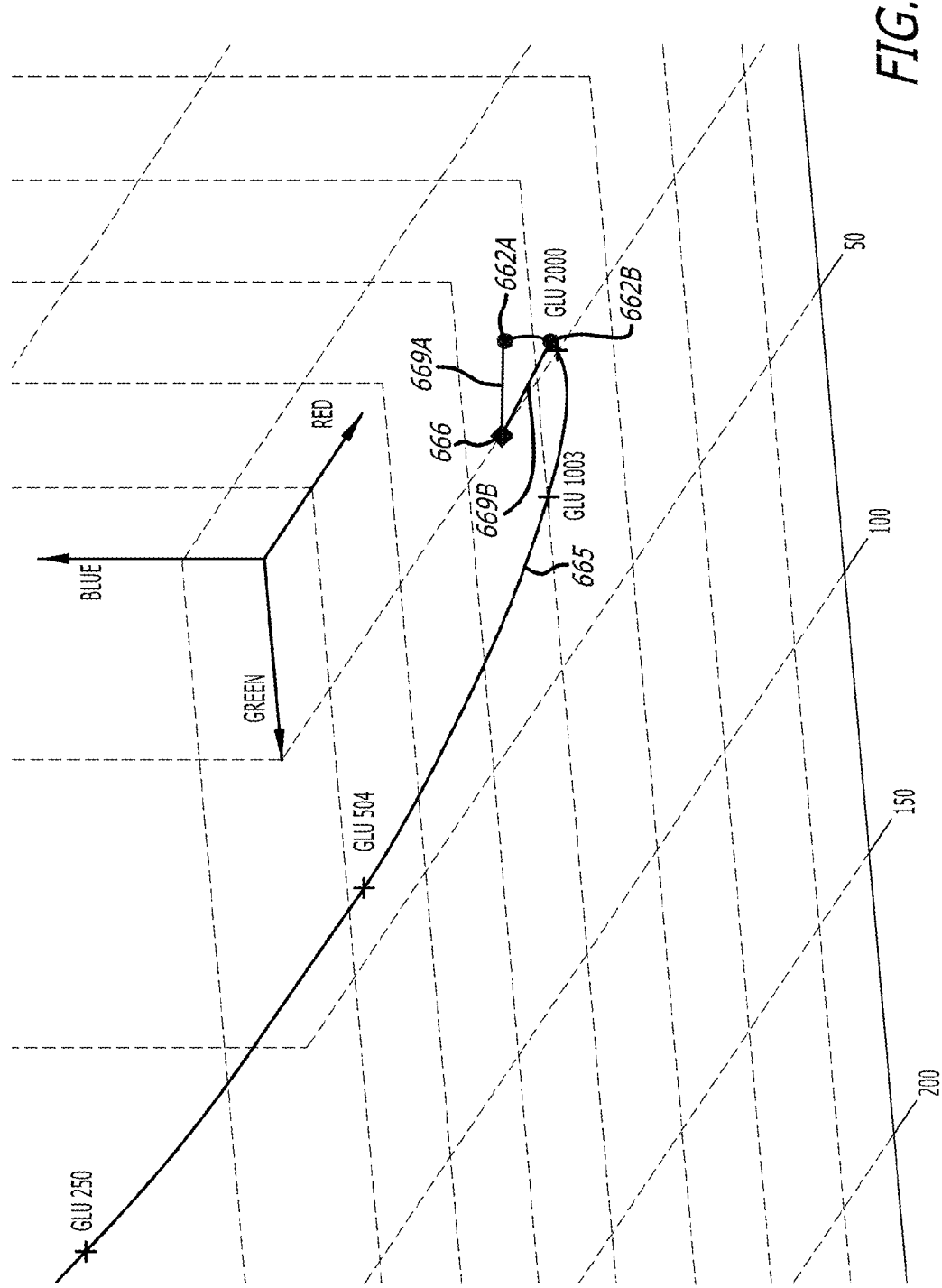
FIG. 6B is a magnified view of a portion of a three dimensional RGB color space graph of an analyte calibration curve.

FIG. 6B illustrates the ambiguity that can arise with a single snapshot at a single time point. In FIG. 6A, the titration point 622 of the resulting analyte being read was determined by a projection 615, the shortest path between the analytical color calibration curve 610 and the measured point 602. Given a single measurement and little curvature in the color calibration curve, this is a fair approximation. These methods prove to work well in most cases. However, in the case of a trajectory along a calibration curve (e.g., a portion of the calibration curve) that has a concave curvature, the resulting analyte titration/concentration may be indeterminate.

A concave curvature in a calibration curve can potentially provide several solutions corresponding to the nearest point. One such well-documented indeterminate example is in high levels of concentrations of glucose. The high concentration level portion (e.g., above five hundred (500) milligrams per deciliter (mg/dl)) of a glucose calibration curve winds around into a segment of an ellipse or a loop.

FIG. 6B illustrates the difficulty to make the right determination of glucose concentration above five hundred (500) mg/dl of glucose. In FIG. 6B, a glucose color calibration curve 665 forms a loop trajectory near its end that is similar to part of an ellipse. Therefore, if a hypothetical measured point 666 is near to the ellipse focal point of the end of the curve 665, the measured point 666 is roughly equidistant to multiple points 662A-662B in the loop. The distances of trajectories 669A-669B from the measure point 666 to points 662A-662B along the calibration curve 665 is substantially similar. Accordingly, either of points 662A-662B may be chosen as the nearest to the measured point 666 and provides different levels of glucose concentration. Thus, use of a single measured point 666 at a single point in time can therefore provide indeterminate or unreliable measurements. It is a well-known that over-the-counter (OTC) consumer devices in the market fail to report adequate or reliable values in the zone near the ellipse focal point of the curve 665. The methods described herein can provide more reliable values.

Time Dimension

Figure 7A:
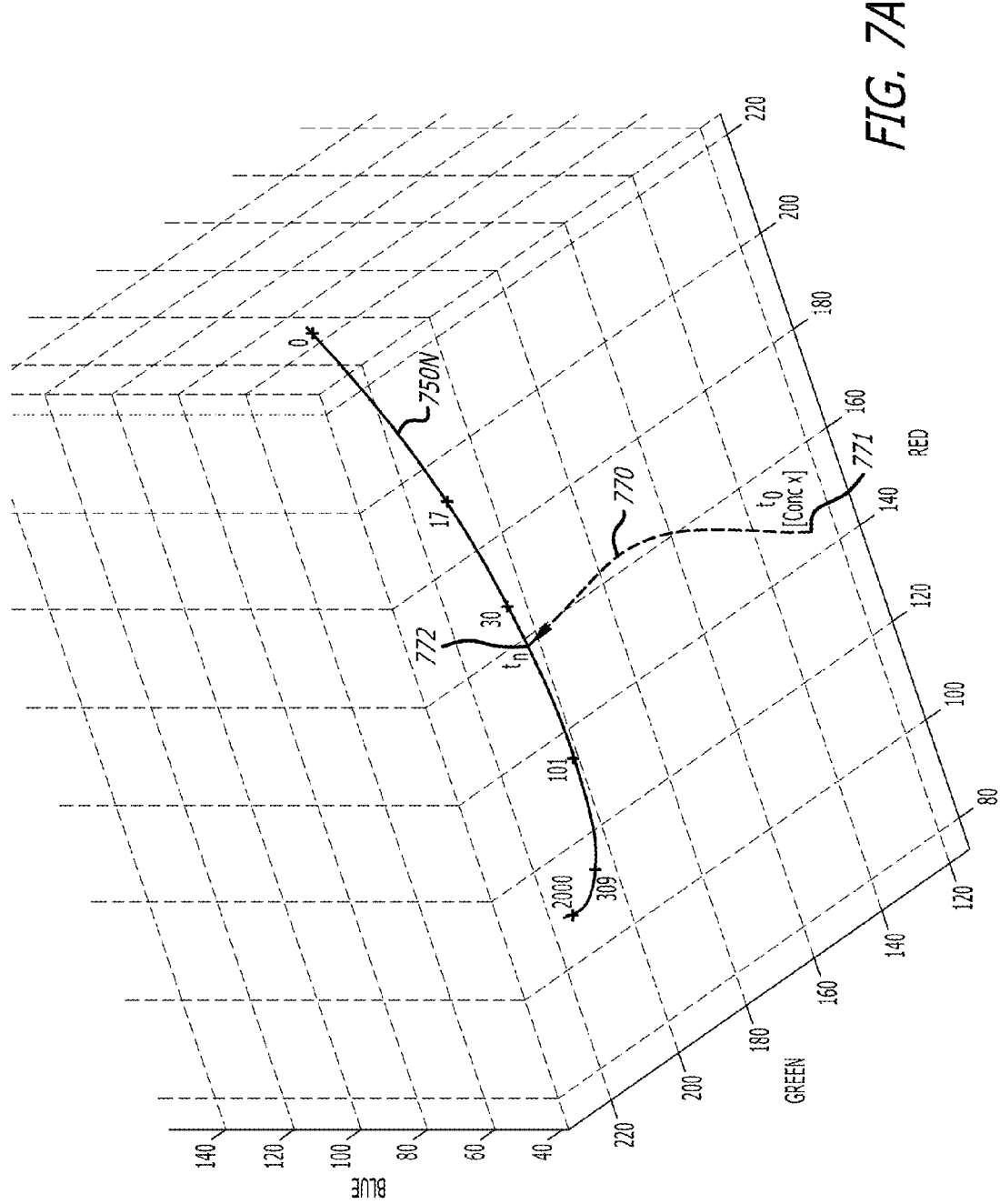
FIG. 7A is a three dimensional RGB color space graph showing a chemical trajectory of an analyte reaction.

Another way of assessing the chemical reaction takes kinetics and time into account. Equations (1), (2) and (3), below, provide a chemical trajectory for an analyte reaction over time. A schematic representation of a chemical trajectory 770N for an Nth analyte reaction over time (from time $t_0$ to $t_n$) is shown in FIG. 7A.

A protein reagent pad is dipped for a few seconds into a biological sample with an analyte of concentration X [Conc X] at time $t_0$. The color of the reagent pad (test pad) is measured at time $t_0$ and reported into the RGB space at measured point 771. The chemical reaction between the reagent of the pad and the analyte in the biological sample continues towards an asymptotic value, according to its kinetics described by equations (1), (2) and (3). Eventually colors stabilize at a final measurement of time, time $t_n$, marking the end of the chemical reaction between the reagent of the pad and the analyte in the biological sample. The final measurement is plotted in the graph shown in FIG. 7A by measured point 772. The measured point 772 is the intersection between the kinetic reaction of the reagent at a final measurement of time and a color calibration curve 750N. The color calibration curve 750N may be provided by the manufacturer of the test pad for a given analyte in the test paddle. The color calibration curve 750N represents the color of the test pad associated with various concentration levels of the analyte at a given time $t_n$. Accordingly, the color calibration curve 750N may also be referred to herein as a color-mass calibration curve. The trajectory 770 between the measured points 771-772 represents the change or evolution of color of the test pad over time, from time $t_0$ to time $t_n$, for a concentration X of a given analyte in a biological sample. Accordingly, the trajectory 770 may also be referred to herein to as a color evolution trajectory.

Formal Definition of Reaction Rate

Consider a Typical Chemical Reaction:

$$aA + bB \rightarrow pP + qQ$$

where the lowercase letters (a, b, p, and q) represent stoichiometric coefficients, while the capital letters represent the reactants (A and B) and the products (P and Q).

According to International Union of Pure and Applied Chemistry's (IUPAC's) Gold Book definition, the reaction rate r for a chemical reaction occurring in a closed system under isochoric conditions, without a build-up of reaction intermediates, is defined by Equation 1 as:

$$r = -\frac{1}{a}\frac{d[A]}{dt} = -\frac{1}{b}\frac{d[B]}{dt} = \frac{1}{p}\frac{d[P]}{dt} = \frac{1}{q}\frac{d[Q]}{dt} \quad \text{Eq. 1}$$

where [X] denotes the concentration of the substance X. The rate of reaction differs from the rate of increase of concentration of a product P by a constant factor (the reciprocal of its stoichiometric number) and for a reactant A by minus the reciprocal of the stoichiometric number. Reaction rate usually has units of moles per liter per second (mol/Ls).

The rate equation or rate law is a mathematical expression used in chemical kinetics to link the rate of a reaction to the concentration of each reactant. Equation 2 illustrates the rate equation:

$$r = k(T)[A]^n[B]^m \quad \text{Eq. 2}$$

In these equations, k(T) is the reaction rate coefficient or rate constant. It includes all the parameters that affect reaction rate, except for concentration, which is explicitly taken into account. Of all the parameters influencing reaction rates, temperature is normally the most important to consider and is accounted for by the Arrhenius equation.

Each reaction rate coefficient k has a temperature dependency, which is usually given by the Arrhenius equation in Equation 3 as follows:

$$k = A \; e^{\left(\frac{-E_a}{RT}\right)} \quad \text{Eq. 3}$$

The numerator Ea of the exponent in Equation 3 is the activation energy and the denominator R is the gas constant. Since at temperature T the molecules have energies given by a Boltzmann distribution, one can expect the number of molecular collisions, with energy greater than the activation energy $E_a$, to be proportional to $$e^{\left(\frac{-E_a}{RT}\right)}.$$

The factor A in Equation 3 is a collisional frequency factor expressed in collisions/seconds. The values for collisional frequency A and activation energy $E_a$ are dependent on the reaction. More complex equations may be used that describe temperature dependence of other rate constants that do not follow this pattern.

Figure 7B:
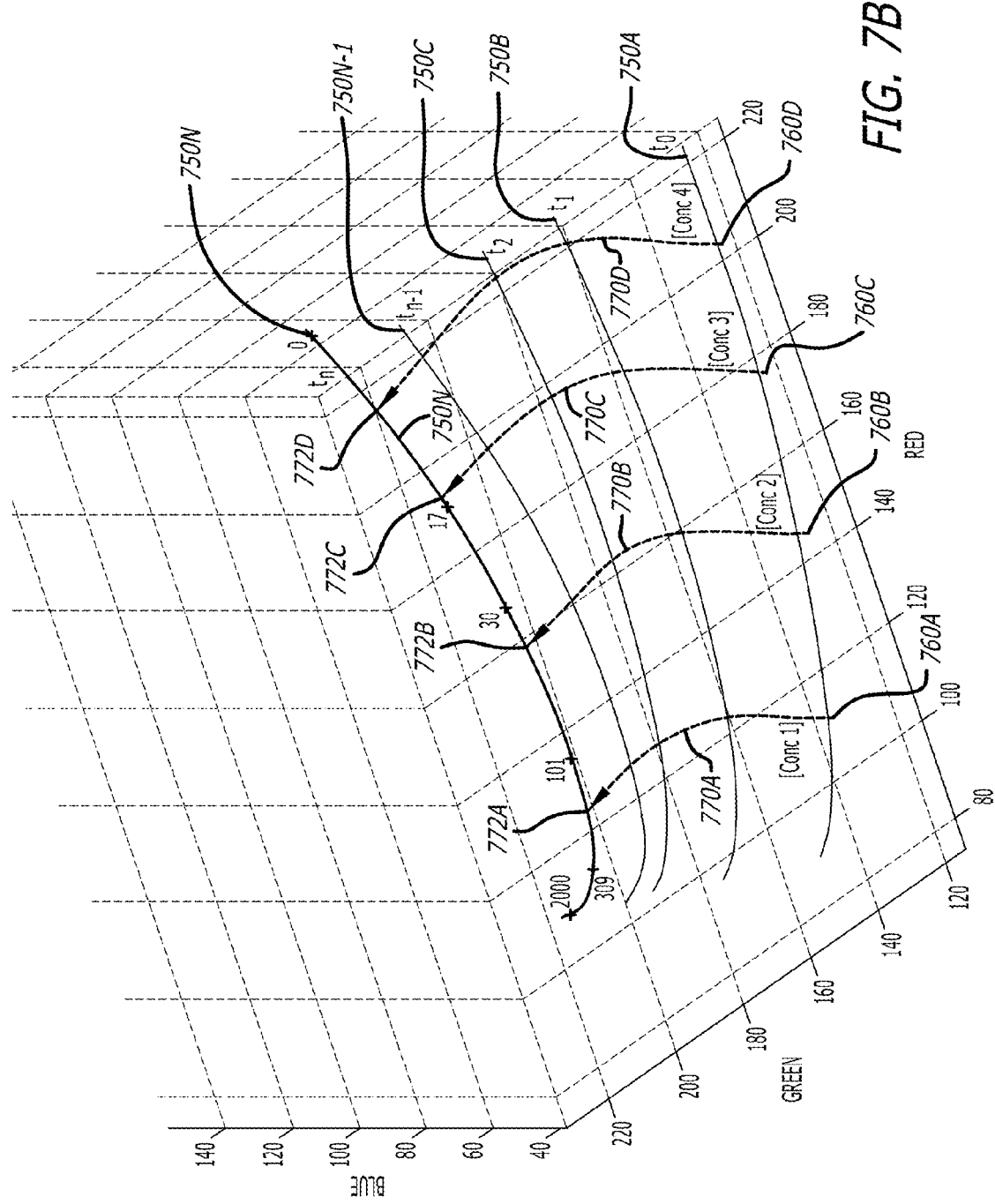
FIG. 7B is a three dimensional RGB color space graph of analyte calibration curves at multiple elapsed times.

Referring now to FIG. 7B, a three dimensional color time evolution graph for a given analyte and test pad is shown. The three dimensional color time evolution graph includes a plurality of color calibration curves 750A-750N in RGB color space for a given analyte over a range of time $t_0$ through tn. The three dimensional color time evolution graph further includes a plurality of color evolution trajectories 770A-770D per concentration in RGB color space for a given analyte. The graph of the color evolution trajectory curves 770A-770D illustrate how different reaction rates for different concentrations [Conc 1] through [Conc 4] of analyte are associated with the color change in RGB color space of a reagent test pad over time.

Given a reagent test pad, various concentrations (e.g., [Conc 1] to [Conc 4]) for an analyte reflect a unique initial color point 760A-760D in the RGB space at time $t_0$ immediately after the urine sample (or other type of sample) is applied. The initial unique colors for the various concentrations form the initial color calibration curve 750A. The initial unique colors of the reagent test pad evolve over time to further form the color calibration curve 750B at time t1 through the color calibration curve 750N at time tn. At time tn, the reagent test pad has reached is final color at a point 772A-772D along the color calibration curve 750N for the various concentrations of analyte. Along color calibration curve 750N, the reaction has reached its asymptote and the color of each test pad has reached its final color level at the point 772A-772D during a testing period.

The color evolution trajectory in time for a given concentration 760 is represented by the curves or trajectories 770A-770D shown by dotted lines in FIG. 7B. Therefore, color evolution trajectories 770A-770D are used by the embodiments of the invention to make accurate predictions of color-time evolution for a given concentration of analyte. Color-time evolution has a one-to-one correspondence to the evolution of the reaction rate k of a mass or concentration of an analyte over time.

FIG. 7B represents color calibration curves 750A-750N for a single reagent test pad and analyte. A similar three dimensional graph with multiple color calibration curves and color evolution trajectories can be formed for other reagent test pads and their respective analyte. For a paddle 100 with twelve test pads, for example, the manufacturer of each reagent test pad may provide twelve different sets of graphs of color calibration curves.

Figure 8:
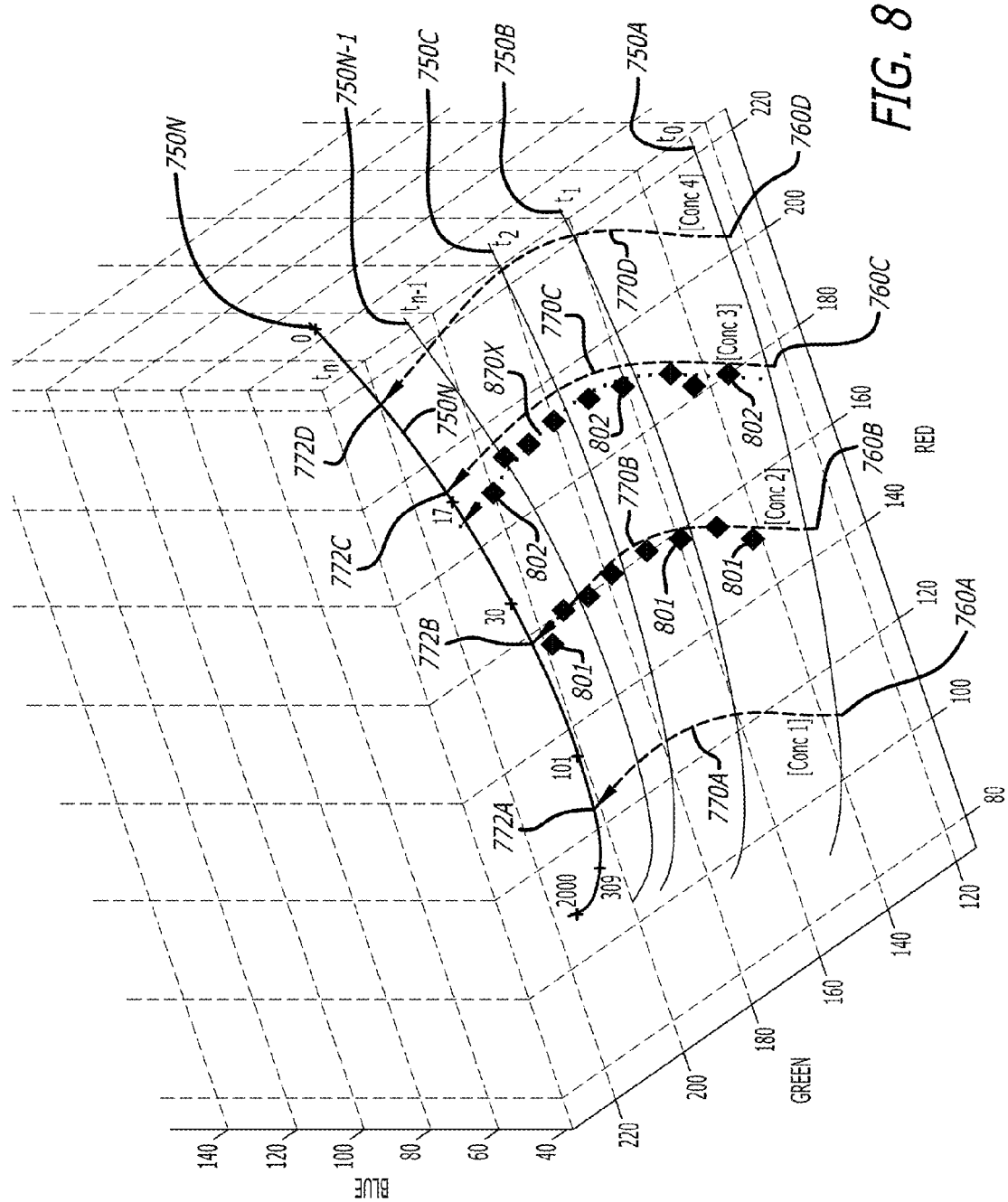
FIG. 8 is a three dimensional RGB color space graph of analyte calibration curves at multiple elapsed times with measured reaction points.

Referring now to FIG. 8, to obtain a curve representing the color-time evolution for a concentration of analyte for a given user, a sequence of pictures (or video) are captured at times t1 through tn. Each picture represents one of a plurality of measurement points in the RGB color space along a color-time evolution curve. For example, a first user with a first concentration of analyte is measured and produces a first sequence of pictures/video over time with a changing color represented by measured points 801 over time. A second user with a second concentration of analyte is measured and produces a second sequence of pictures/video of the test pad on the paddle over time with a changing color represented by measured points 802 over time from $t_0$ through tn.

Since most of the chemical reactions of the test paddle 100 take sixty seconds or less, a sampling rate of six images per second would provide three-hundred-sixty (360) measurement points between time $t_0$ and time tn. The sequence of measurement points 801 along a color time evolution curve 770B for example, can be fit to the saturating Michaelis-Menten equations to determine a concentration of the reacting analyte, as is now discussed.

If A is the unknown concentration of an analyte, B is a reagent with known concentration, and AB is the results of a chemical reaction leading to binding/activating/revealing of a colorimetric probe Col, giving a color that is proportional to the concentration of A, one has the following kinetic scheme:

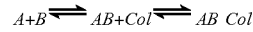

where $$[ABCol] = \frac{[AB]_0[Col]}{K_d + [Col]}$$

and $K_d$ is the apparent dissociation constant of the final colorimetric reaction.

One can derive the analyte concentrations in an analytical or graphical manner. From an analytical standpoint, the colorimetric probe [Col] is known from the chemical specifications of the CTP. The dissociation constant $K_d$ is derived from the color time-resolved curve 870X is formed by the measured points 802 over time, for example. The value for the product [ABCol] in the equation is determined by the color measurement of a test pad made by the automated test apparatus capturing the color images, such as the through heads up display glasses or a smartphone/tablet computer. With all but one unknown in the equation, the concentration of the reacting analyte [AB] can be derived analytically from the rearranged equation:

$$\frac{(K_d + [Col])[ABCol]}{[Col]} = [AB]_0$$

In practice by means of a graphical manner, with a color calibration graph including a plurality of color calibration curves, the concentration of the reacting analyte in the sample is directly accessible by the intersection between a color-time evolution trajectory (aka, a time-resolved trajectory) 870X and the color calibration curves 750A-750N over time.

The sequence of measured color points 802 over time can also be approximated by a polynomial, a quadratic curve, a bspline, or any other fitting model. Such curves build the color-time evolution trajectory 870X corresponding to the precise concentration [X] measured by the analyte pad.

A plurality of known concentrations can be used to generate a plurality of know color-time evolution trajectories corresponding to known concentrations or masses in a biological sample measured by the analyte pad. FIG. 7B, for example, illustrates a plurality of color-time evolution trajectories 770A-770D of an analyte pad for known or given mass or concentrations 760 of an analyte in a biological sample, including concentration 1 (Conc 1), concentration 2 (Conc 2), concentration 3 (Conc 3), and concentration 4 (Conc 4).

Assuming a hypothetical number of three-hundred and sixty measurements of color for a test pad over time, the precision of the concentration [X] of analyte is about nineteen times more precise than a single measurement obtained from a single image.

Additionally, the fundamental principle of computing concentrations can be improved by directly determining the mathematical intersection between the color-time evolution trajectory 870X corresponding to the concentration [X] and the color calibration curve 750N at the final point in time tn. This intersection (or the nearest points between two trajectories) is unique for each concentration [X]. The embodiments of the invention avoid the principle of using a minimal distance from a point to the trajectory (as shown in FIG. 6A) and the issues of indeterminations as shown in FIG. 6B and described herein. The embodiments of the invention that employ the color calibration graph including a plurality of color calibration curves, can also focus on the optimal reaction times for each specific chemical reaction pad.

Cross-Referencing Analyte Reactions to Further Increase Accuracy

The color calibration curves 750A-750N over time for a given analyte are determined at a given calibration temperature $T_0$ and acidity $pH_0$. In the field of use, the biological sample (e.g., urine) being tested is likely to have a different temperature and a different acidity, referred to herein as measured temperature TM and measured acidity pHM. Compensating for the different temperatures and acidity can lead to improved results.

The paddle 100 includes multiple pads that are concurrently changing in color over the same time sample periods. Pictures are concurrently captured for each test pad with a given color at the same moment in time (same reaction time t) from the same biological sample. The various data for each test pad may be fused together or cross-referenced in a manner to provide improved accuracy for the analyte reactions. With a sequence of multiple approximation curves reflecting the color-time evolution trajectories 770A-770D of each of the i analyte pads (e.g., i=12 in one embodiment) at a given concentration [Xi], equations (1), (2) and (3) allow for increasing the precision of the outcome by equating the following constant parameters across analyte pads:

same reaction time t
same temperature T
same acidity pH

It is known that chemical reaction pathways vary as a function of the temperature T and the acidity pH. Those two variables may serve as correcting inputs, both of which can be derived from a plurality of analyte pads.

For a set of different analyte pads whose reactants and reactions are known, the $Q_{10}$ (temperature dependency of said reactions) are different.

The temperature dependency of different reactions $Q_{10}$ is the ratio of the rate constants at two different temperatures normalized for a difference of ten (10) degrees Fahrenheit as provided in the equation that follows:

$$Q_{10} = \left(\frac{k_2}{k_1}\right)^{\frac{10}{T_2-T_1}}$$

The variables $T_1$ and $T_2$ are the two different temperatures, the constants $k_1$ and $k_2$ are the rate constants at those respective temperatures where the first temperature is less than the second temperature ($T_1 < T_2$).

Following those different reactions in time, gives rise to a set of curves to be understood as a system of equations whose pattern can be ascribed to a common temperature. A difference in temperature influences those different chemical reaction rates in different ways. Hence, the temperature may be derived for the parallel chemical reactions.

In this case, reaction rates also depend on acidity pH. The acidity pH of a biological sample may be directly readable from a specific chemical test pad CTP of the paddle 100 selected to test for acidity.

Temperature can effect a reaction in two ways, either by a direct effect on the reaction rate constant or by denaturing an eventual enzyme at high temperatures. The effect of the temperature on the rate constant is given by the Arrhenius equation;

$$k = A \, e^{\left(\frac{-E_a}{RT}\right)}$$

where $E_a$ is the activation energy, R the gas constant, T the absolute temperature and A the collision factor for the reacting chemicals.

Knowing the temperature T, one can either analytically or empirically solve the problem of the temperature difference between calibration and user testing for the time-resolved trajectories 770A-770D.

Knowing acidity pH, the activity of protons in a reacting solution can influence all the other reactions that would be obtained in parallel. If the proton is needed for a chemical reaction or binding, increasing the proton concentration will accelerate the chemical reaction. If a proton is generated by a chemical reaction, the opposite effect will occur—increasing the proton concentration will decelerate the chemical reaction.

The acidity pH value may be directly determined from its own chemical test pad (CTP). Knowing the acidic value, the influence of acidity pH on the non-pH related reactions can be either derived analytically or solved graphically with the appropriate calibration curves.

In FIG. 8, the trajectory 870X is determined from the measured color values 802 generated by the chemical reaction between the biological sample and an analyte for a given user over time. The trajectory 870X is an approximation curve of the color-time evolution trajectory corresponding to the concentration [X] that is being more precisely measured the analyte pad.

The trajectory or curve 750N in FIG. 8 is the final color calibration curve representing the RGB colors of all concentrations of the same analyte at the final time tn, the end of the chemical reaction between the biological sample and the analyte. Trajectory of the calibration curves 750A-750N are established with known initial parameters at time $t_0$, such as calibration temperature $T_0$, and calibration acidity $pH_0$ of the calibration sample during the calibration period of the test pad of the paddle 100 by the manufacturer.

The test paddle and its test pads may not have the same final measured reaction time tn as that used in forming the calibration curves. The reaction time for concentration X will differ somewhat from reaction time for the calibration concentrations [Conc 1] through [Conc 4]. Furthermore, the measure time and calibration times may also be somewhat out of synchronization. For example, the final measured time may be 58 seconds while the final calibration time was 60 seconds. It would be desirable to compensate for the variation in reaction time and synchronization, by adjusting the final calibration curve 750N. Alternatively, the measured samples may be shifted in time or interpolated to form the trajectory 870X to intersect with the time frame of the calibration curves spontaneously on the fly.

The calibration curves 750A-750N are for specific times $t_0$ through tn, respectively. The initial calibration time $t_0$ represents the calibration time point for measuring initial color of a test pad just after being exposed to a biological sample, such as urine. The calibration curve 750A is determined by using a plurality of biological samples of differing known concentrations and measuring the color of the reagent test pad at the same calibration time $t_0$. The calibration time $t_1$ represents the next time point that color of the test pad is measured after the test pad has been exposed to the plurality of biological samples of different known concentrations. The final calibration time $t_n$ represents the last time point that color of the test pad is measured after the test pad has been exposed to the plurality of biological samples of different known concentrations.

Furthermore, a more accurate measured concentration for an analyte may be determined by compensating the final calibration curve 750N for the difference between measured temperature TM and calibration temperature $T_0$, as well as the difference between measured acidity pHM and calibration acidity $pH_0$.

Figure 9:
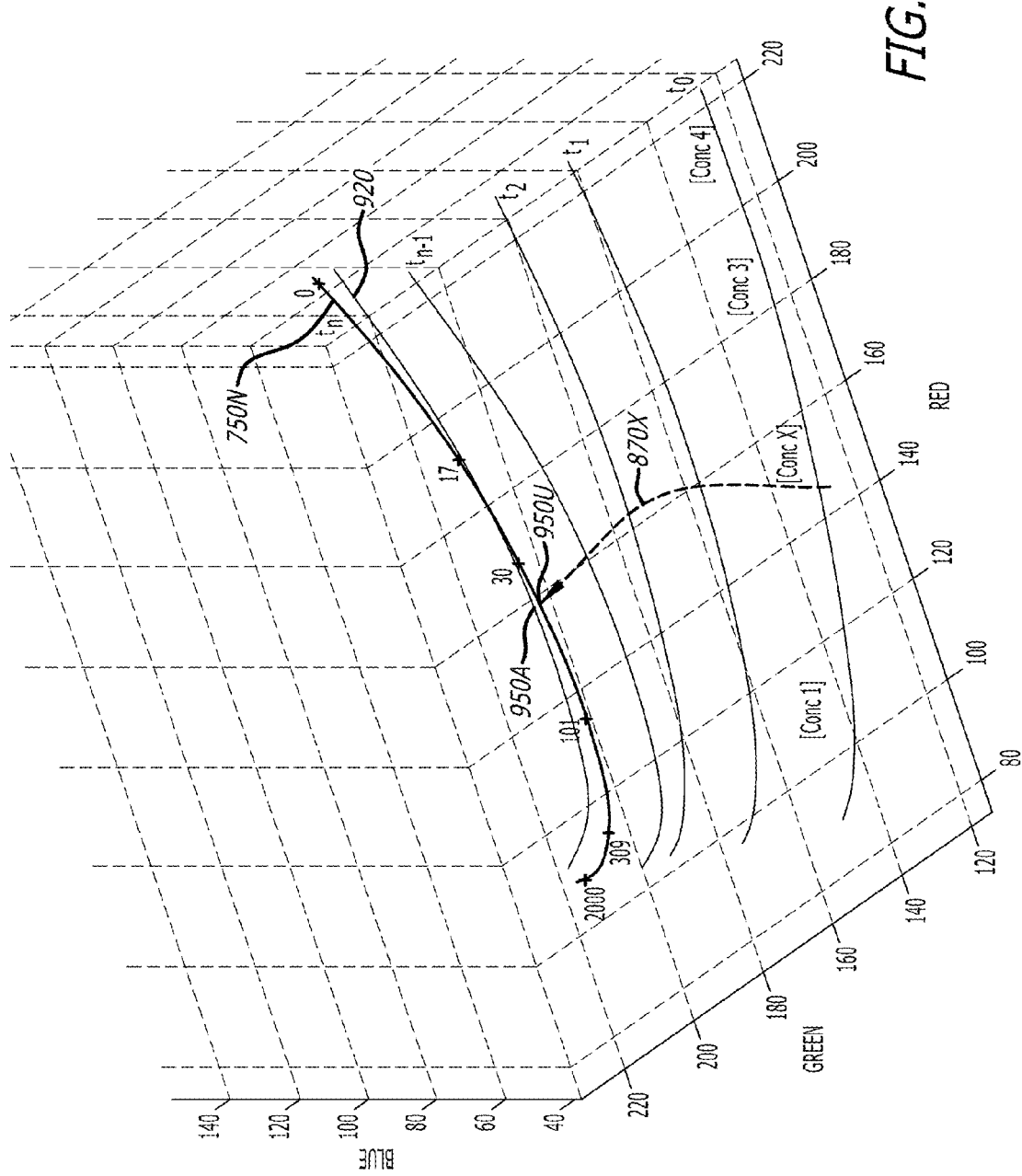
FIG. 9 is a three dimensional RGB color space graph of analyte calibration curves correcting for time, temperature and acidity (pH).

In FIG. 9, the final calibration curve 750N may be adjusted for the difference between measured acidity pHM and calibration acidity $pH_0$ to form an acidity corrected calibration curve. A specific chemical test pad (CTP) on the paddle may be used to determine the measured acidity pHM in a biological sample and thus may be referred to as a calibration test pad. The calibration curves 750A-750N are established with known initial parameter for acidity, a calibration acidity $pH_0$ of the calibration sample during the calibration period of the test pad of the paddle 100 by the manufacturer.

The final calibration curve 750N may also be, or alternatively be, adjusted to correct for the difference between a measured temperature TM and the calibration temperature $T_0$. The measured temperature TM, the ambient temperature where the measurement is taken, is derived from one or more test pads or from the computer or glasses that may have an ambient temperature sensor. The calibration curves 750A-750N are established with known initial parameter for temperature, a calibration temperature $T_0$ of the calibration sample during the calibration period of the test pads of the paddle 100 by the manufacturer.

In FIG. 9, a fully corrected calibration curve 920 is shown. The fully corrected calibration curve 920 represents the correction of the calibration curve 750N for differences between the calibration and measured/experimental conditions, including that of the measured temperature TM, and/or the measured acidity pHM corresponding to the experimental conditions used to collect the points 802 that form trajectory 870X.

Without correction or adjustment, an unadjusted intersection point 950U is formed at the intersection between the measured trajectory 870X and the color calibration curve 750N. With the corrections for time, temperature, and acidity pH, the method gains in accuracy because it adjusts the intersection between the measured trajectory 870X and the corrected color calibration curve 920 to the corrected or adjusted intersection point 950A. The corrected or adjusted intersection point 950A is a more reliable data point to obtain a titration or concentration of an analyte.

CONCLUSION

When implemented in software, the elements of the embodiments of the invention are essentially the code segments or instructions executed by a processor (e.g., processor 1006 in FIG. 10B or processor 1104 in FIG. 11) to perform the necessary tasks. The program or code segments can be stored in a processor readable medium. The "processor readable medium" may include any medium that can store information (e.g., memory 1008 in FIG. 10B or memory 1105 in FIG. 11). Examples of the processor readable medium include an electronic circuit, a semiconductor memory device, a read only memory (ROM), a flash memory, an erasable programmable read only memory (EPROM), a floppy diskette, a CD-ROM, an optical disk, a hard disk, a fiber optic medium, a radio frequency (RF) link, etc. The program or code segments may be downloaded from another storage device using a computer data signal embodied in a carrier wave over a transmission medium or a communication link. The computer data signal may include any signal that can propagate over a transmission medium such as electronic network channels, optical fibers, air, electromagnetic, RF links, etc. The code segments may be downloaded via computer networks such as the Internet, Intranet, etc.

While certain exemplary embodiments have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art. For example, the embodiments shown and described herein describe analytes of reagent test pads for urinalysis of urine. The embodiments of the invention can function and be performed with analytes of reagent test pads for the analysis of blood. Accordingly, the embodiments of the invention should not be construed as being limited by such illustrated embodiments, but rather construed according to the claims that follow below.

What is claimed is:

1. A method comprising:
   applying a biological sample to a plurality of test pads of a test paddle;
   capturing images over periods of time of the plurality of test pads of the test paddle as different reagents of the test pads react to the biological sample;
   quantifying each color of the plurality of test pads in each of the captured images over time;
   determining a color trajectory over time for each test pad of the plurality of test pads;
   comparing the color trajectory with calibration curves to determine analyte concentration for one or more of the plurality of test pads; and
   displaying results of the analyte concentration to a user in response to the comparison.

2. The method of claim 1, further comprising:
   determining temperature and acidity (pH) of a chemical reaction between the biological sample and a test pad.

3. The method of claim 2, further comprising:
   before determining the color trajectory, correcting the calibration curves to account for effects of one or more of a reaction time, the temperature, and the acidity (pH).

4. The method of claim 1, wherein
the biological sample is urine or blood.

5. An apparatus for automatic test diagnosis of a biological sample with a test paddle, the apparatus comprising:
a personal computing device including:
a camera to capture images over time of test pads of a test paddle;
a processor coupled to the camera, the processor to analyze color over time of each test pad;
determine a color trajectory over time for each test pad;
compare the color trajectory for each test pad with associated color calibration curves for each test pad to determine analyte concentrations in a biological sample;
and
a display device coupled to the processor, the display device to display results of the analyte concentrations to a user in response the comparison.

6. The apparatus of claim 5, wherein
the personal computing device is a head mounted device.

7. The apparatus of claim 6, wherein
the head mounted device includes one of a heads-up-display, contact lenses, corrective lenses, and monocles.

8. The apparatus of claim 5, wherein the personal computing device includes
an eyeglass frame; and
wherein the display device is a small video display device coupled to the eyeglass frame;
wherein the camera is a small camera coupled to the eyeglass frame.

9. The apparatus of claim 5, wherein the personal computing device includes
an eyeglass frame with a left eyeglass and a right eyeglass; and
wherein the display device is a small video projector coupled to the eyeglass frame to project a display on either the left eyeglass or the right eyeglass to display the results of the analyte concentration to the user;
wherein the camera is a small camera coupled to the eyeglass frame.

10. A method comprising:
(a) applying a known concentration of an analyte in a biological sample of a predetermined acidity to a test pad at a predetermined temperature;
(b) capturing color images over a plurality time points of the test pad as it reacts to the biological sample;
(c) quantifying a color of the test pad in each of the captured color images at each of the plurality of time points;
repeating steps (a) through (c) for a plurality of differing concentrations of the analyte in a plurality of biological samples for one or more test pads; and
plotting along a curve in three dimensions of color space coordinates of a color graph, the quantified color for each respective time point for the plurality of concentrations of analyte to form a plurality of color calibration curves respectively associated with the plurality of time points.

11. The method of claim 10, further comprising:
(d) applying a known concentration of the analyte in a biological sample of a known acidity to a test pad at a known temperature;
(e) capturing color images over known periods of time of the test pad as it reacts to the known concentration of analyte in the biological sample;
(f) quantifying a color of the test pad in each of the captured color images at each known period of time; and
(g) plotting a plurality of the quantified colors of the test pad in the color graph over time.

12. The method of claim 11, further comprising:
interpolating between each quantified color of the test pad in the color graph to form a color evolution trajectory associated with the known concentration of analyte to intersect with the plurality of color calibration curves.

13. The method of claim 12, further comprising:
applying a second biological sample with an unknown concentration of analyte to a second test pad;
capturing color images of the test pad at measured time points as it reacts to the unknown concentration of analyte in the second biological sample;
quantifying each color of the test pad in each of the captured color images at each measured time point from a first measured time point to a last measured time point; and
determining a concentration of an analyte in the second biological sample in response to one or more quantified colors of the test pad at one or more measured time points.

14. The method of claim 10, wherein
the color space coordinates are red, green, and blue colors of a red-green-blue color space.

15. A method comprising:
applying a biological sample with an unknown concentration of analyte to a test pad;
capturing color images of the test pad at measured time points as it reacts to the unknown concentration of analyte in the biological sample;
quantifying each color of the test pad in each of the captured color images at each measured time point from a first measured time point to a last measured time point; and
determining a concentration of an analyte in the measured biological sample in response to one or more quantified colors of the test pad at one or more measured time points.

16. The method of claim 15, wherein
the determining of the concentration of the analyte in the biological sample includes determining an intersection point between a color evolution trajectory and a final color calibration curve.

17. The method of claim 15, wherein
the determining of the concentration of the analyte in the biological sample includes
plotting a plurality of quantified colors of the test pad in a color graph over a plurality of measured time points.

18. The method of claim 15, further comprising:
determining a measured acidity and a measured temperature associated with the biological sample;
correcting for differences in acidity and temperature between the measured acidity of the biological sample and the measured temperature associated with the biological sample and a calibration acidity of one or more calibration samples and a calibration temperature associated with the one or more calibration samples.

19. The method of claim 18, wherein
the differences are corrected by forming an adjusted final color calibration curve.

20. The method of claim 15, wherein
the concentration of analyte in the measured biological sample is determined by finding one or more intersections of a color evolution trajectory associated with the concentration of the analyte in the measured biological sample with a plurality of color calibration curves.

21. The method of claim 15, wherein the biological sample is urine or blood.

* * * * *